United States Patent
Feng

(10) Patent No.: US 9,654,234 B2
(45) Date of Patent: May 16, 2017

(54) SYSTEM AND METHOD FOR AUTOMATICALLY TIME LABELING REPETITIVE DATA

(71) Applicant: Focus Ventures, Inc., Santa Monica, CA (US)

(72) Inventor: Shuo Feng, Fullerton, CA (US)

(73) Assignee: Focus Ventures, Inc., Santa Monica, CA (US)

( * ) Notice: Subject to any disclaimer, the term of this patent is extended or adjusted under 35 U.S.C. 154(b) by 0 days.

(21) Appl. No.: 15/249,115

(22) Filed: Aug. 26, 2016

(65) Prior Publication Data

US 2017/0063475 A1 Mar. 2, 2017

Related U.S. Application Data

(60) Provisional application No. 62/211,513, filed on Aug. 28, 2015, provisional application No. 62/213,003, filed on Sep. 1, 2015, provisional application No. 62/293,658, filed on Feb. 10, 2016, provisional application No. 62/338,016, filed on May 18, 2016,
(Continued)

(51) Int. Cl.
*A63B 24/00* (2006.01)
*H04B 17/15* (2015.01)
*H04L 12/26* (2006.01)
*H04B 14/02* (2006.01)

(52) U.S. Cl.
CPC ......... *H04B 17/15* (2015.01); *A63B 24/0003* (2013.01); *A63B 24/0062* (2013.01); *H04B 14/026* (2013.01); *H04L 43/028* (2013.01)

(58) Field of Classification Search
CPC A63B 24/0003; A63B 24/0062; G08B 13/00; G08B 21/0211; G08B 21/0461; G08B 25/006; G08B 25/008; H04B 17/20; H04B 17/23
USPC ........................................................ 375/316
See application file for complete search history.

(56) References Cited

U.S. PATENT DOCUMENTS

| | | | |
|---|---|---|---|
| 9,448,763 B1 * | 9/2016 | Dziuk | ................ A63B 24/0062 |
| 2008/0001735 A1 | 1/2008 | Tran | |
| 2013/0162525 A1 | 6/2013 | Ye et al. | |

(Continued)

OTHER PUBLICATIONS

PCT International Search Report and Written Opinion for PCT/US16/49077, Nov. 28, 2016, 12 pages.
(Continued)

*Primary Examiner* — David S Huang
(74) *Attorney, Agent, or Firm* — Fenwick & West LLP

(57) ABSTRACT

An exercise assistance system labels sensor signals received from a movement measurement device to identify repetitions within the sensor signals. The movement measurement device can transmit motion data describing the user's movement to the exercise assistance system, and includes the sensor signals generated by one or more sensors in the movement measurement device. The exercise assistance system generates a combination signal from the received sensor signals and passes the combination signal through a low pass filter to generate a labeling signal. The exercise assistance system can generate three types of labels for the labeling signal identifying different parts of repetitions. The exercise assistance system labels the sensor signals using the generated labels and can identify repetitions in the labeled sensor signals using a classification model.

20 Claims, 13 Drawing Sheets

Related U.S. Application Data provisional application No. 62/355,528, filed on Jun. 28, 2016.

(56) References Cited

U.S. PATENT DOCUMENTS

| | | |
|---|---|---|
| 2014/0275821 A1 | 9/2014 | Beckman |
| 2014/0278219 A1 | 9/2014 | Canavan et al. |
| 2015/0100141 A1 | 4/2015 | Hughes |
| 2015/0153374 A1 | 6/2015 | Balakrishnan et al. |
| 2016/0093196 A1* | 3/2016 | Shinar ............... A61B 5/6892 340/565 |
| 2016/0342686 A1* | 11/2016 | Garmark ........... G06F 17/30743 |

OTHER PUBLICATIONS

PCT International Search Report and Written Opinion for PCT/US16/049076, Nov. 30, 2016, 8 pages.

* cited by examiner

SYSTEM AND METHOD FOR AUTOMATICALLY TIME LABELING REPETITIVE DATA

CROSS REFERENCE TO RELATED APPLICATION

This application claims the benefit of U.S. Provisional Application No. 62/211,513, filed on Aug. 28, 2015, U.S. Provisional Application No. 62/213,003, filed Sep. 1, 2015, U.S. Provisional Application No. 62/293,658, filed Feb. 10, 2016, U.S. Provisional Application No. 62/338,016, filed May 18, 2016, and U.S. Provisional Application No. 62/355,528, filed Jun. 28, 2016, each of which is herein incorporated by reference.

BACKGROUND

Field of the Invention

This disclosure relates generally to signal analysis and more specifically to the detection of a repetition within a signal.

Description of Art

Sensors, such as accelerometers, can be used to generate signals of physical motion, which can include repetitive motion. Repetitions can be described as periodic transitions from one state for another. For example, if a signal represents a person performing push-up exercises, the repetitions can represent the user transitioning from a position with their arms straight to a position with their arms bent and then back to the first, straight-arm position. These repetitions can be represented by cycles in periodic curves within the signals, such as sinusoids and Fourier series.

The detection of repetitions within signals of real world data is conventionally difficult because the signals can contain noise that obscures the repetitions in the signal. For example, a signal of the person performing the push-ups can be made noisy by the person shaking, inaccuracies in a sensor capturing the push-up motion, or by the person's inconsistency in performing the push-ups. Thus, simply locating local extrema within the signal can be inaccurate, especially in situations where multiple repetitions are not performed continuously, since the extrema may not exist in the signal in these cases.

The difficulty in identifying repetitions within a signal impacts exercise assistance systems, which automatically provide exercise advice and guidance to users. By being unable to identify repetitions in signals describing user movement, conventional exercise assistance systems often can only provide general guidance that does not address the particularities of an individual user's performance of an exercise.

SUMMARY

An exercise assistance system labels sensor signals received from a movement measurement device to identify repetitions within the sensor signals. The movement measurement device can be a wearable device worn by a user and can transmit motion data describing the user's movement to the exercise assistance system. The motion data includes the sensor signals generated by one or more sensors in the movement measurement device.

The exercise assistance system generates a combination signal from the received sensor signals. The combination signal is a combination of the sensor signals that accentuates the repetitions within the sensor signals. Example combinations of sensor signals include summing the sensor signals and summing the sensor signals in quadrature. The exercise assistance system passes the combination signal through a low pass filter to generate a labeling signal. The low pass filter smooths the combination signal by removing high frequency noise from the combination signal without removing the frequencies that represent the repetitions. In some embodiments, the cutoff frequency for the low pass filter is established based on an upper bound for the frequency of the repetitions to ensure that the repetitions are not filtered out of labeling signal.

The exercise assistance system generates labels for the labeling signal. Each label can identify a part of a repetition and can include a timestamp that identifies where in the labeling signal the part of the repetition occurs. The exercise assistance system can generate three types of labels. Type 1 labels identify the beginning of a repetition, type 2 labels identify an extremum of a repetition, and type 3 labels identify the end of a repetition. Type 2 labels can be generated by identifying local extrema in the labeling signal and type 1 and type 3 labels can be generated by identifying local extrema in a first order derivative of the labeling signal.

The exercise assistance system determines label triplets of the labels generated for the labeling signal. A label triplet includes a type 1 label, a type 2 label, and a type 3 label that are chronologically sequential in the labeling signal. The exercise assistance system labels the sensor signals using the determined label triplets. The exercise assistance system may label the sensor signals by generating labels that correspond to the labels generated for the labeling signal with timestamps that correspond to the labels for the labeling signal.

The exercise assistance system identifies repetitions in the sensor signals based on the labeled sensor signals. In some embodiments, the exercise assistance system uses a classification model to identify label triplets as repetitions or as noise. The exercise assistance system can train the classification model using features extracted from labeled sensor signals and using repetitions that were manually labeled by humans.

By identifying repetitions in sensor signals, the exercise assistance system can ensure that a user is properly following an exercise routine specified by a personal trainer or a physical therapist. The exercise assistance system can also analyze the identified repetitions to determine if the user is performing the exercise correctly. Additionally, the identification of type 1 labels, type 2 labels, and type 3 labels provides for more effective identification of repetitions in cases where repetitions are not well defined and provides for additional accuracy in cases where repetitions are not performed continually.

BRIEF DESCRIPTION OF THE DRAWINGS

The figures depict various embodiments of the present invention for purposes of illustration only. One skilled in the art will readily recognize from the following discussion that alternative embodiments of the structures and methods illustrated herein may be employed without departing from the principles of the invention described herein.

FIG. 13 B illustrates a method for applying a classification model for identifying repetitions in labeled sensor signals, in accordance with some embodiments.

DETAILED DESCRIPTION

The features and advantages described in the specification are not all inclusive and, in particular, many additional features and advantages will be apparent to one of ordinary skill in the art in view of the drawings and specification. Moreover, it should be noted that the language used in the specification has been principally selected for readability and instructional purposes, and may not have been selected to delineate or circumscribe the inventive subject matter.

Example System Environment

Figure 1:
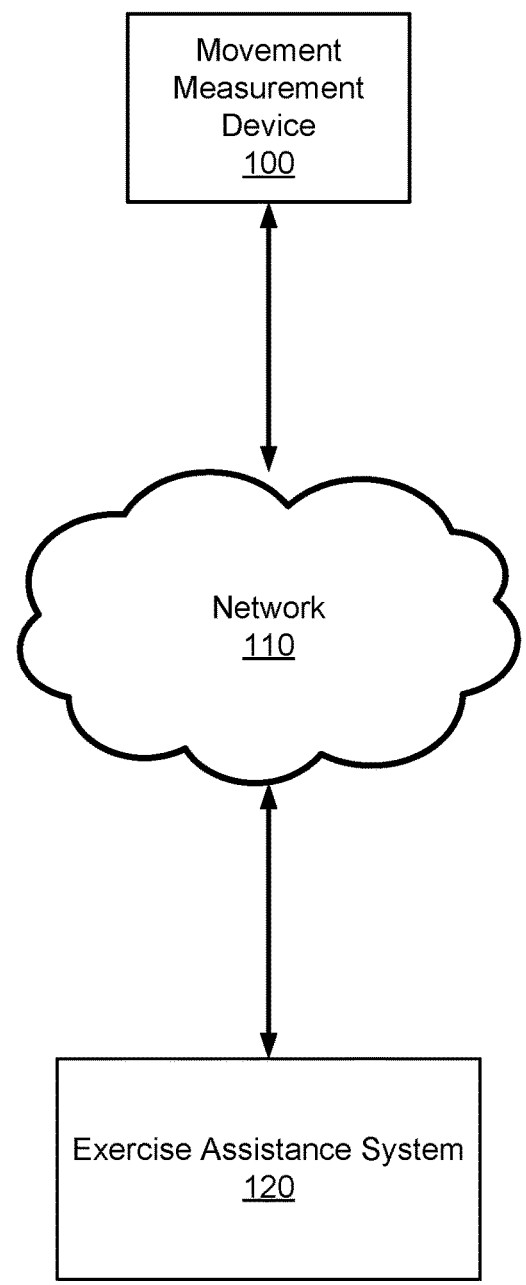
FIG. 1 illustrates an example system environment for an exercise assistance system, in accordance with some embodiments.

FIG. 1 illustrates an example system environment for an exercise assistance system, in accordance with some embodiments. FIG. 1 includes a movement measurement device 100, a network 110, and an exercise assistance system 120. Alternate embodiments can include additional, fewer, or different components than those illustrated in FIG. 1 and the functionality of the components may be divided up differently from the description below. For example, while only one movement measurement device 100 is illustrated in FIG. 1, alternate embodiments can include a plurality of movement measurement devices 100 in communication with the exercise assistance system 120 through the network 110.

The movement measurement device 100 collects motion data describing a user's movement and transmits the motion data to the exercise assistance system 120. The movement measurement device 100 can be a wearable device, such as a smart watch, a fitness bracelet/anklet, or a headset. In some embodiments, the movement measurement device 100 communicates with a personal computing device (e.g., a smart phone, a tablet, a personal computer) to transmit the motion data to the exercise assistance system 120. The movement measurement device 100 includes one or more sensors to generate the motion data, such as an accelerometer, a gyroscope, a GPS module, a magnetometer, or an electronic compass. The one or more sensors of the movement measurement device 100 generate one or more sensor signals to be included in the motion data. For example, an accelerometer in the motion measurement device 100 may generate a sensor signal that describes the acceleration of the movement measurement device 100 over time. In some embodiments, the movement measurement device 100 processes the motion before transmitting the motion data to the exercise assistance system 120. For example, the movement measurement device 100 may encrypt, compress, or reformat the motion data.

The movement measurement device 100 can communicate with the exercise assistance system 120 via the network 110, which may comprise any combination of local area and wide area networks employing wired or wireless communication links. In one embodiment, the network 110 uses standard communications technologies and protocols. For example, the network 110 includes communication links using technologies such as Ethernet, 802.11, worldwide interoperability for microwave access (WiMAX), 3G, 4G, code division multiple access (CDMA), digital subscriber line (DSL), Bluetooth, etc. Examples of networking protocols used for communicating via the network 110 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 110 may be represented using any format, such as hypertext markup language (HTML) or extensible markup language (XML). In some embodiments, all or some of the communication links of the network 110 may be encrypted.

The exercise assistance system 120 provides exercise guidance and advice to a user based on motion data received from the movement measurement device 100. The exercise assistance may be provided to the user through the movement measurement device 100 or through a personal computing device, such as a computer, a laptop, a tablet, or a phone. The exercise assistance system 120 can provide instructions to a user for how to perform an exercise and can identify, based on the motion data, whether the user is performing the exercise correctly. To determine whether the user is performing the exercise correctly, the exercise assistance system 120 identifies repetitions of the exercise that are performed by the user. Methods that can be used by the exercise assistance system 120 are described below. The exercise assistance system 120 may store motion data from the motion measurement device 100. The stored motion data may include motion data collected from the user of the motion measurement device 100, other users of the exercise assistance system 120, and motion data from third party systems. In some embodiments, the exercise assistance system 120 stores historical motion data.

Time Labeling Repetitive Data

Figure 2:
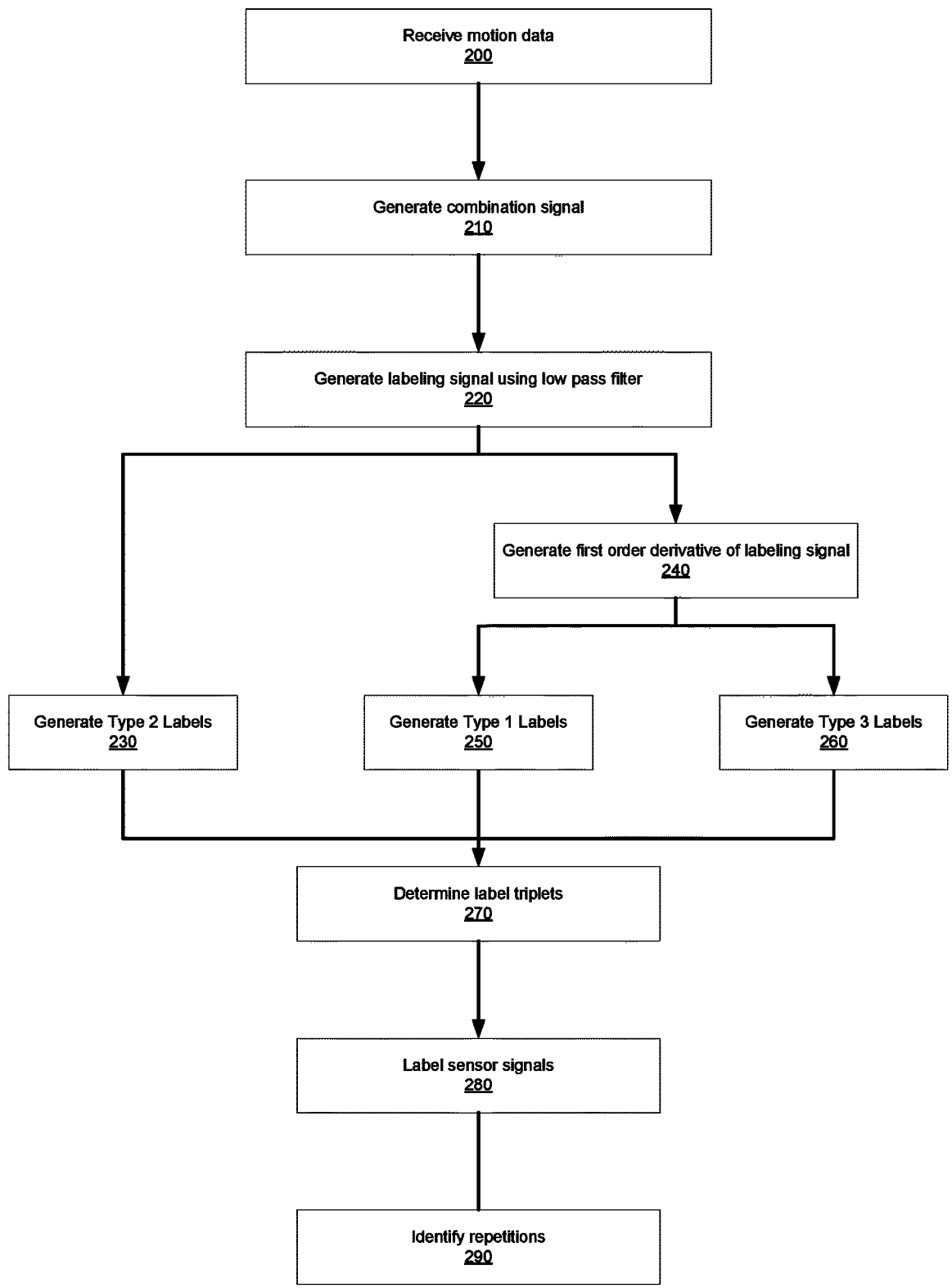
FIG. 2 is a flowchart of a method for labeling repetitions in sensor signals, in accordance with some embodiments.

FIG. 2 is a flowchart of a method for labeling repetitions in sensor signals, in accordance with some embodiments. Alternate embodiments may include more, fewer, or different steps from the steps illustrated in FIG. 2, and the steps may be performed in a different order from the order described herein.

For the discussion below, the exercise assistance system 120 is used as an example system performing an embodiment of a method for time labeling repetitions within sensor signals. However, the described method may be used for any purpose where repetitions within a signal may need to be labeled. For example, a system may use the methods described herein to label repetitions within a signal describing electrical voltage, heat, sound, pressure, light, or any other physical phenomenon. Additionally, a system can use the methods described herein to identify instances of any physical motion of a user, such as workplace motions (e.g. lifting boxes, getting up from a desk), sports motions (e.g. swinging a baseball bat, throwing a ball, tackling another player), or motions indicative of an emergency (e.g. the user falling down, the user being in a car crash, the user firing a gun).

Figure 3:
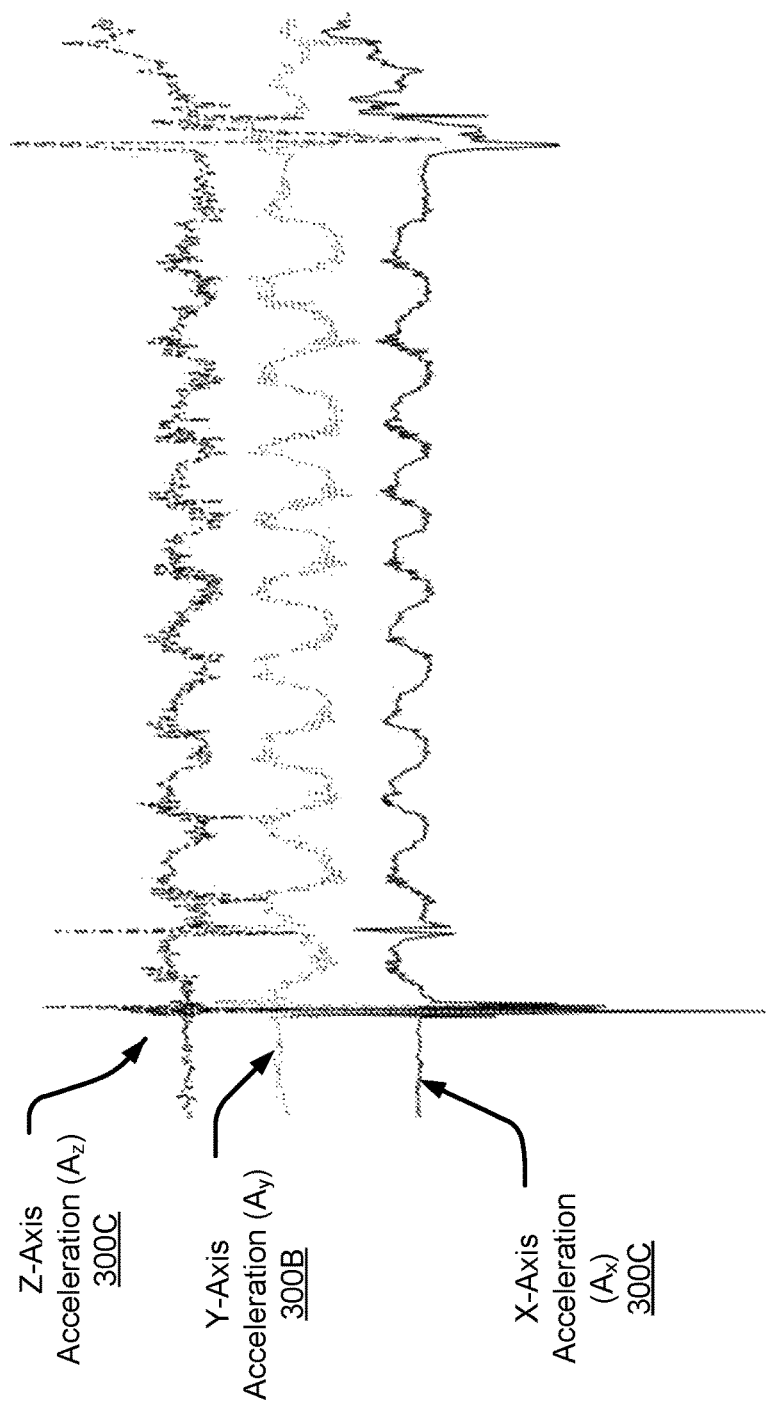
FIG. 3 illustrates example sensor signals from the motion measurement device, in accordance with some embodiments.

The exercise assistance system 120 receives 200 motion data from a movement measurement device 100 that includes one or more sensor signals from one or more sensors in the motion measurement device 100. The sensor signals describe repetitive motion of a user performing an exercise, such as push-ups, pull-ups, crunches, etc. FIG. 3 illustrates example sensor signals from the motion measurement device 100, in accordance with some embodiments. FIG. 3 shows sensor signals from a three dimensional accelerometer, including an x-axis acceleration signal 300A, a y-axis acceleration signal 300B, and a z-axis acceleration signal 300C.

The exercise assistance system 120 can generate 210 a combination signal from the sensor signals in the motion data. The combination signal can be a combination of one or more sensor signals 300 that accentuates the repetitions in the sensor signals 300. For example, for sensor signals about push-ups, the combination signal may accentuate movement or acceleration along an axis perpendicular to the ground more than an axis parallel to the ground. In some embodiments, the exercise assistance system 120 selects a combination from a set of combinations, and selects the combination that provides a combination signal with the greatest variance. Possible combinations, using accelerometer sensor signals of FIG. 3 as an example, include:

$\pm A_x$
$\pm A_y$
$\pm A_z$
$\pm(A_x+A_y)$
$\pm(A_x-A_y)$
$\pm(A_x+A_z)$
$\pm(A_x-A_z)$
$\pm(A_y+A_z)$
$\pm(A_y-A_z)$
$\pm\sqrt{A_x^2+A_y^2+A_z^2}$ where $A_x$, $A_y$, and $A_z$ denote the raw data from accelerometer the x-axis acceleration signal 300A, the y-axis acceleration signal 300B, and the z-axis acceleration signal 300C respectively. Similar combinations apply to other sensor signals. The potential combinations are not limited to the lists above. For example, Euclidean sum, Eigenvector decomposition, and principle component analysis can also be used. In some embodiments, the combination of sensor signals may be selected based on the computational intensity of the combination. For example, if a complex combination allows for better time labeling of repetitions but at a great computational cost, the exercise assistance system 120 may select a combination that provides for worse labeling accuracy, but that is simpler to compute.

Figure 4:
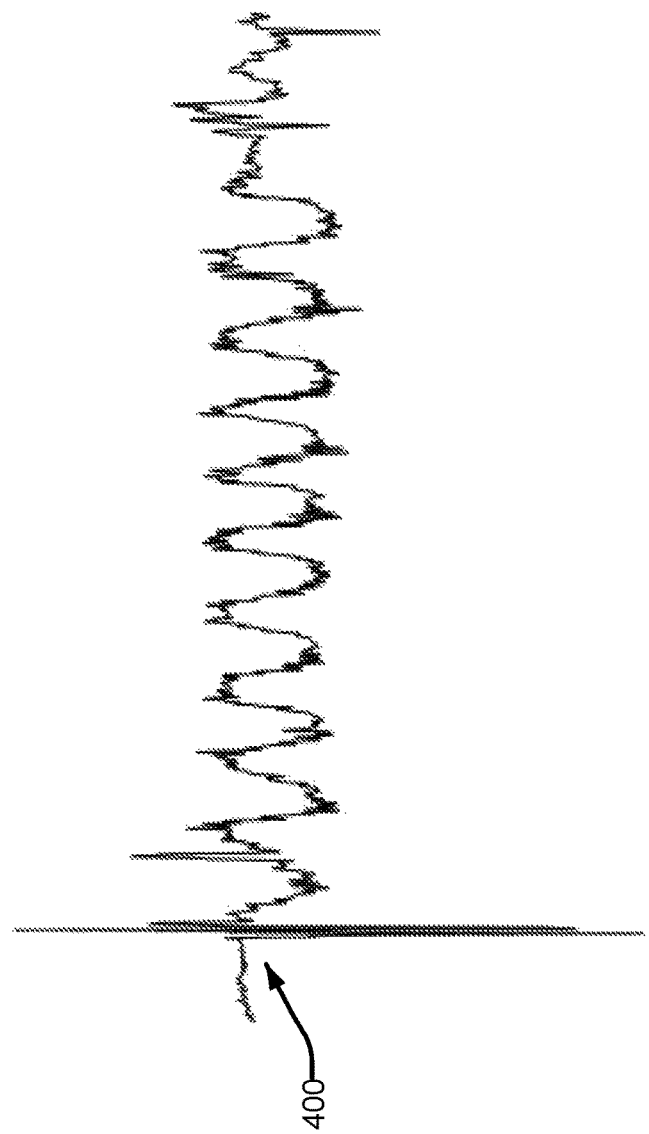
FIG. 4 illustrates a combination signal of sensor signals, in accordance with some embodiments.

FIG. 4 illustrates a combination signal 400 of the sensor signals in FIG. 3, in accordance with some embodiments. The combination illustrated in FIG. 4 is based on data from multiple accelerometers.

Figure 5:
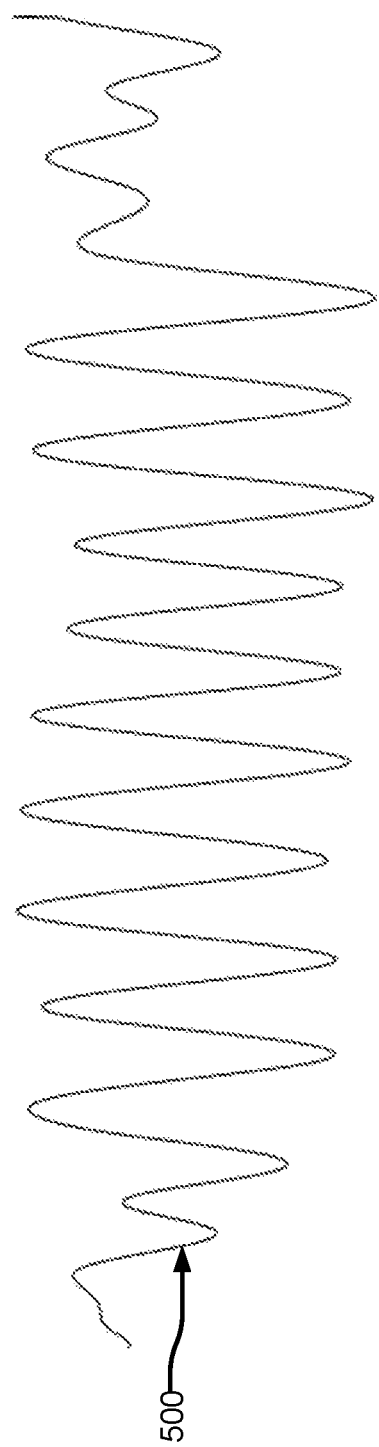
FIG. 5 illustrates a labeling signal, in accordance with some embodiments.

The exercise assistance system 120 generates 220 a labeling signal by passing the combination signal 400 through a low pass filter. The low pass filter is used to reduce the noise of the labeling signal and smooths the curve of the combination signal. Thus, each repetition of the motion of interest may be represented by a single valley or peak of the labeling signal. The low pass filter removes frequencies from the combination signal that are above a cutoff frequency. In some embodiments, a typical range for the cutoff frequency of the low pass filter is from 0.5 Hz to 5 Hz. The low pass filter should have a cutoff frequency that is higher than an upper bound for the repetition frequency so that every repetition shows up clearly in the labeling signal. For example, if the fastest repetition frequency is found to be two repetitions per second, then the low pass filter should have a cutoff frequency higher than two Hertz (i.e. two cycles per second). The cutoff frequency for the low pass filter can be determined based on statistics of the motion of interest from motion data stored by the exercise assistance system 120. For example, the exercise assistance system 120 may use the stored motion data to determine the fastest repetition rate to establish the cutoff frequency for the low pass filter. FIG. 5 illustrates a labeling signal 500, in accordance with some embodiments.

The exercise assistance system 120 can label repetitions in the sensor signals 300 from the motion measurement device 100 using the labeling signal 500. To label repetitions in the labeling signal 500, the exercise assistance system 120 labels the beginning, end, and extremum of each repetition in the labeling signal 500. Each label includes a timestamp that describes when the corresponding part of the repetition occurs in the labeling signal 500. The exercise assistance system 120 labels the labeling signal 500 with three types of labels. Type 1 and type 3 labels represent the beginning and end of a repetition respectively, and type 2 labels represent an extremum (i.e. a minimum or maximum value) of the repetition.

Figure 6:
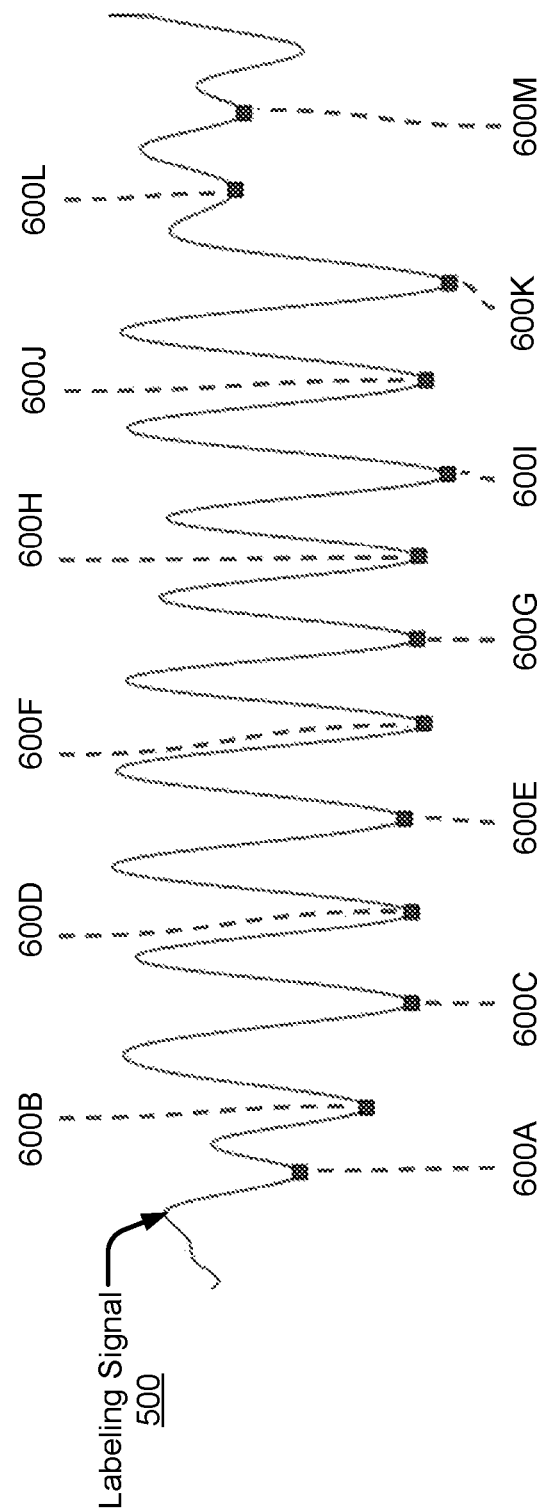
FIG. 6 illustrates a labeling signal labeled with type 2 labels, in accordance with some embodiments.

The exercise assistance system 120 can generate 230 the type 2 labels for the labeling signal 500 by identifying local extrema in the labeling signal 500. FIG. 6 illustrates a labeling signal 500 labeled with type 2 labels 600, in accordance with some embodiments. In the embodiment illustrated in FIG. 6, the exercise assistance system 120 identifies local minima of the labeling signal 500 as type 2 labels 600. However, in other embodiments, the exercise assistance system 120 may identify local maxima in the labeling signal 500 as type 2 labels 600. The exercise assistance system 120 may identify local extrema using gradient descent/ascent.

Figure 7:
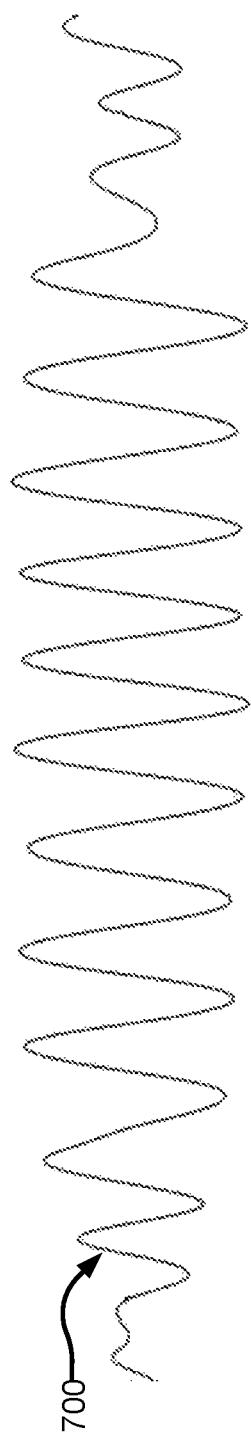
FIG. 7 illustrates a first order derivative signal of a labeling signal, in accordance with some embodiments.

To identify type 1 and type 3 labels for the labeling signal 500, the exercise assistance system 120 generates 240 a first order derivative of the labeling signal 500. The exercise assistance system 120 can generate the first order derivative signal by determining the differences between each pair of consecutive points of the labeling signal 500 and generating the first order derivative signal from those differences. FIG. 7 illustrates the first order derivative signal 700 of the labeling signal 500, in accordance with some embodiments.

Figure 8:
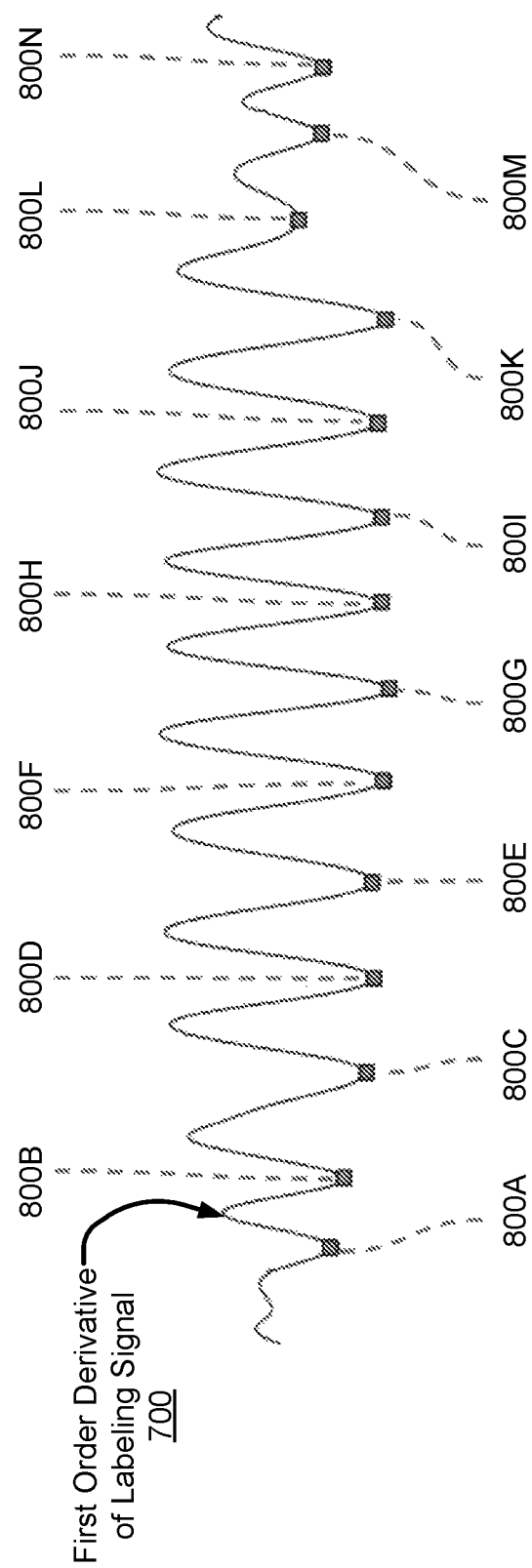
FIG. 8 illustrates a first order derivative signal labeled with type 1 labels, in accordance with some embodiments.
Figure 9:
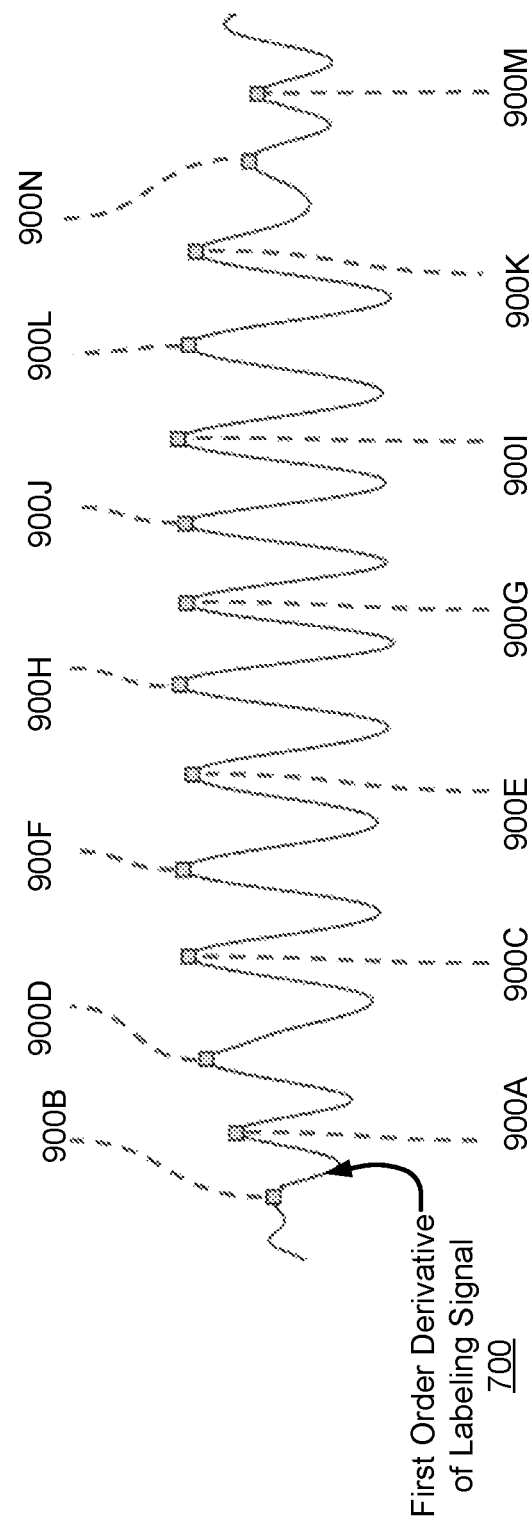
FIG. 9 illustrates a first order derivative signal labeled with type 3 labels, in accordance with some embodiments.

The exercise assistance system 120 generates 250 type 1 labels and generates 260 type 3 labels based on the first order derivative signal 700. To generate type 1 and type 3 labels, the exercise assistance system 120 identifies extrema of the first order derivative signal 700. FIG. 8 illustrates a first order derivative signal 700 labeled with type 1 labels 800, in accordance with some embodiments. FIG. 9 illustrates a first order derivative signal 700 labeled with type 3 labels 900, in accordance with some embodiments. In the embodiments illustrated by FIG. 8 and FIG. 9, the exercise assistance system 120 identifies local minima of the first order derivative signal 700 as type 1 labels 800 and local maxima of the first order derivative signal 700 as type 3 labels 900. In other embodiments, the exercise assistance system 120 identifies local maxima of the first order derivative signal 700 as type 1 labels 800 and local minima of the first order derivative signal 700 as type 3 labels 900. In some embodiments, the exercise assistance system 120 uses the first order derivative signal 700 to determine type 2 labels 600, such as by determine when the first order derivative signal 700 goes from negative to positive or vice versa.

The exercise assistance system 120 can use a sliding window to identify extrema in the labeling system 500 and first order derivative signal 700. The exercise assistance system 120 may use the sliding window to identify an extremum within the fixed range of the sliding window. In some embodiments, the width of the sliding window is substantially equal to the inverse of the cutoff frequency of the low pass filter applied to the combination signal, thereby ensuring that only one repetition exists within the sliding window at a time.

Figure 10:
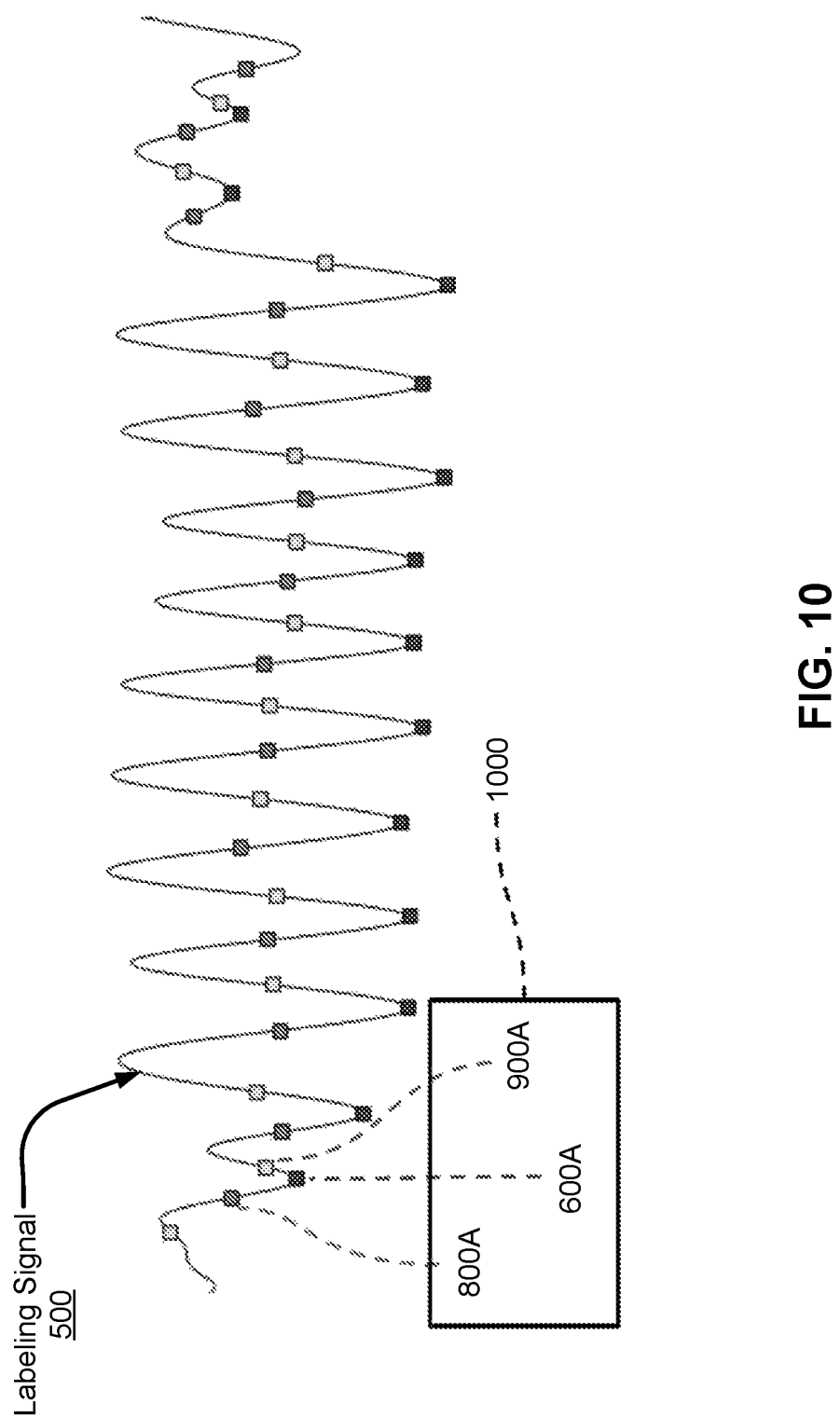
FIG. 10 illustrates sequential labels on a labeling signal, in accordance with some embodiments.

The exercise assistance system 120 determines 270 label triplets to label repetitions in the labeling signal. FIG. 10 illustrates label triplets on the labeling signal 500, in accordance with some embodiments. The exercise assistance system 120 can determine label triplets 1000 from the type 1 labels 800, the type 2 labels 600, and the type 3 labels 900. A label triplet 1000 can include a type 1 label, a type 2 label, and a type 3 label that are chronologically sequential. For example, the label triplet 1000 illustrated in FIG. 10 includes type 1 label 800A, type 2 label 600A, and type 3 label 900A.

The exercise assistance system 120 labels 280 the sensor signals 300 based on the determined sequential labels. The exercise assistance system 120 can label the sensor signals 300 with type 1, type 2, and type 3 labels that correspond to type 1, type 2, and type 3 labels applied to the labeling signal 500 as illustrated in FIG. 10. In some embodiments, the exercise assistance system 120 uses timestamps of each of the labels of the labeling signal 500 to apply the labels with corresponding timestamps to the sensor signals 300. For example, if the labeling signal 500 is labeled with a type 1 label at time t, each sensor signal 300 may also be labeled with a type 1 label at time t.

Figure 11:
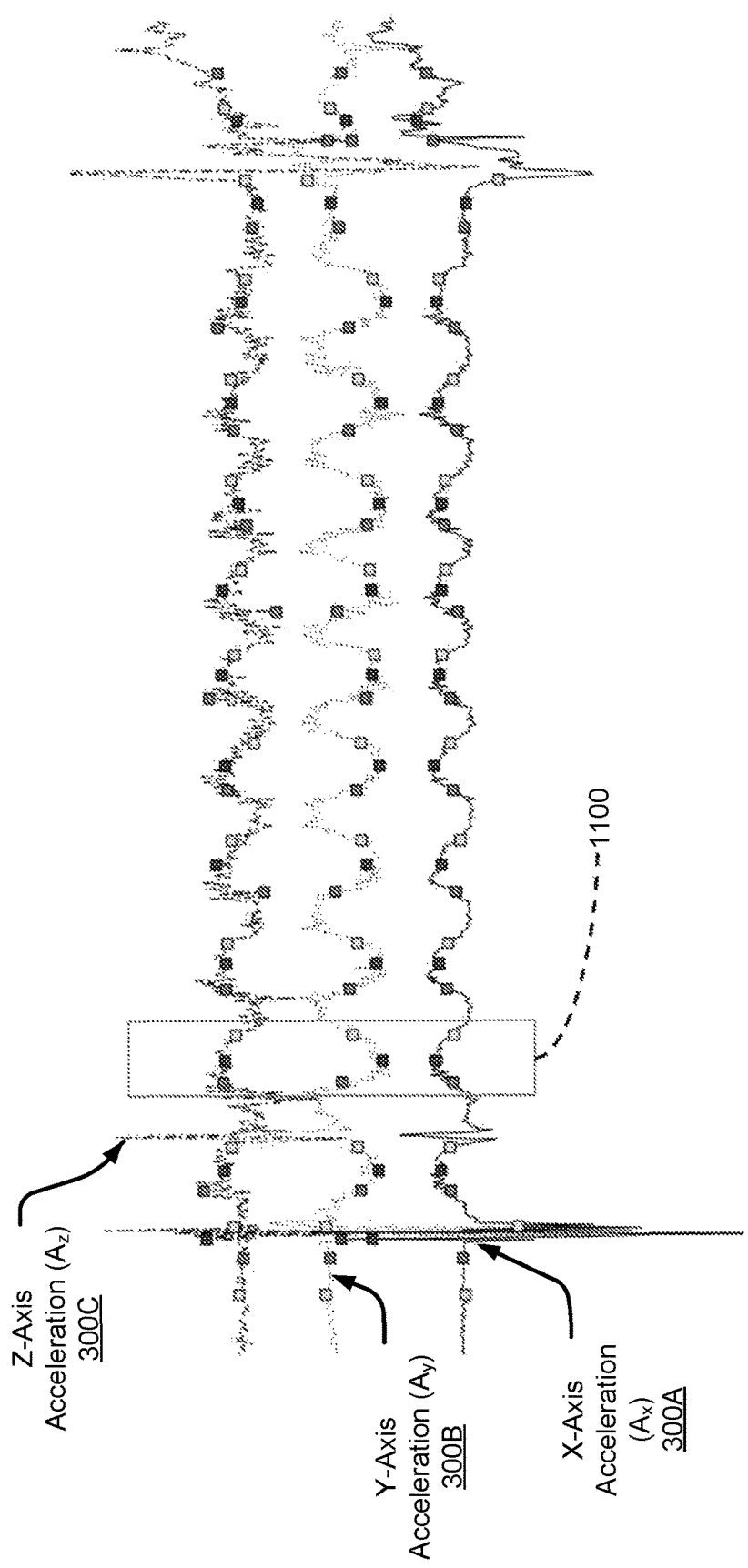
FIG. 11 illustrates labeled sensor signals, in accordance with some embodiments.

FIG. 11 illustrates labeled sensor signals 300, in accordance with some embodiments. Label triplet 1100 corresponds to a label triplet from the labeling signal 500.

Figure 12:
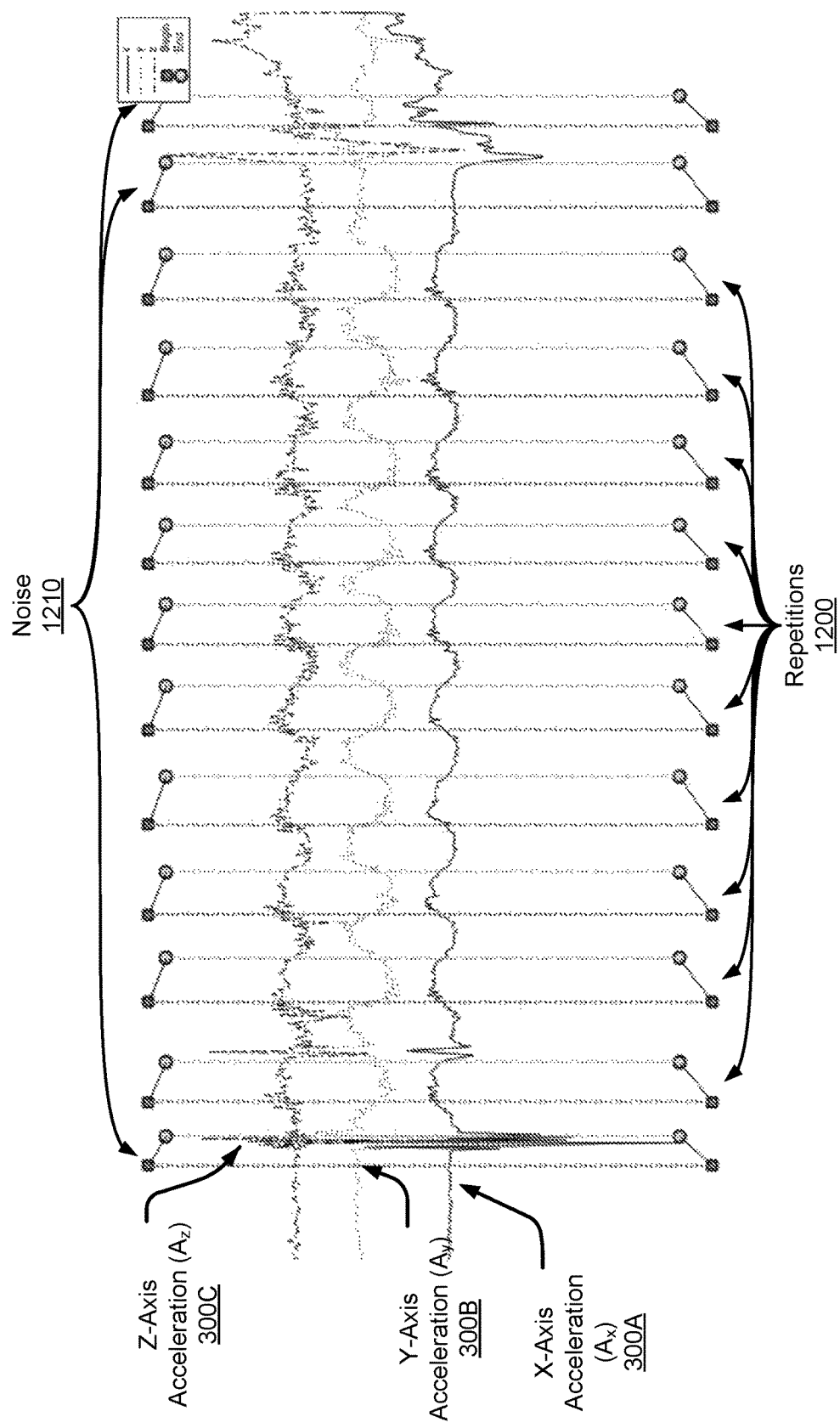
FIG. 12 illustrates identified repetitions and noise within labeled sensor signals, in accordance with some embodiments.

The exercise assistance system 120 identifies 290 repetitions based on the labeled sensor signals 300. In some embodiments, the exercise assistance system 120 favors false positives over false negatives, and thus identifies all label triplets as repetitions. The exercise assistance system 120 may also identify some label triplets as noise rather than as repetitions if it determines that the label triplet is likely not to be a repetition. The exercise assistance system 120 also can identify the beginning and the end of each repetition in the sensor signals 300. FIG. 12 illustrates identified repetitions 1200 and noise 1210 within labeled sensor signals 300, in accordance with some embodiments. Methods for identifying repetitions 1200 and noise 1210 in labeled sensor signals 300 are further described below.

The exercise assistance system 120 can send the identified repetitions 1200 to the user through a personal computing device (e.g. a laptop, desktop, phone, tablet) or through the movement measurement device 100. The exercise assistance system 120 may also use the identified repetitions to identify the motion of interest or to monitor the user's progress in physical therapy.

Identifying Repetitions in Labeled Sensor Signals

Figure 13B:
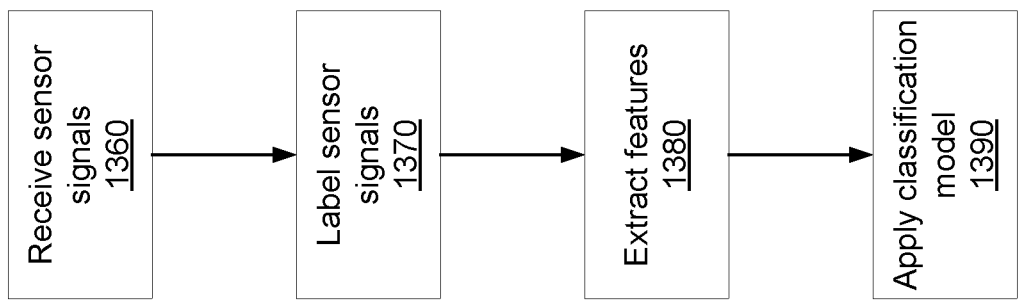
FIG. 13 A illustrates a method for training a classification model for identifying repetitions in labeled sensor signals, in accordance with some embodiments.
Figure 13A:
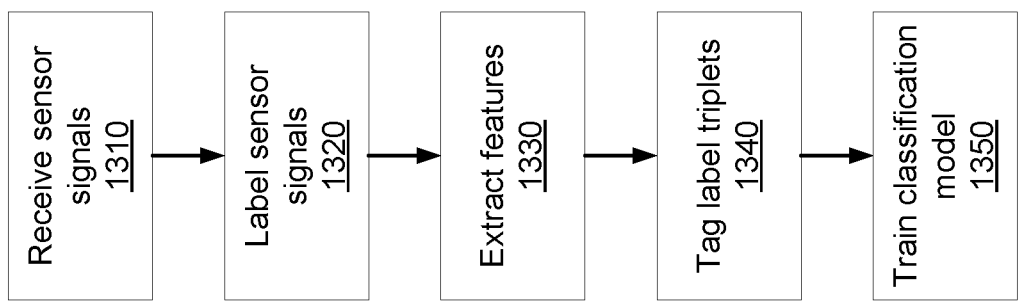

FIG. 13A illustrates a method for training a classification model for identifying repetitions in labeled sensor signals, in accordance with some embodiments. Alternate embodiments may include more, fewer, or different steps from the steps illustrated in FIGS. 13A, and the steps may be performed in a different order from the order described herein.

The exercise assistance system receives 1310 motion data containing sensor signals from a movement measurement device 100 and labels 1320 the sensor signals in accordance with the embodiments described above.

The exercise assistance system extracts 1330 features from the labeled sensor signals. The extracted features may include statistical information about the sensor signals, including average values of the sensor signals, average values of local extrema, median values of local extrema, global extremum values, occurrence counts of local extrema, and covariance and cross correlation between multiple sensor signals. The extracted features also may include information about the sensor signals, such as the frequency composition of the sensor signals, the frequency composition of a corresponding labeling signal, the combination used to generate a corresponding combination signal, and the type of sensor used to generate the sensor signals. Furthermore, the extracted features may include information about the time labels, such as average repetition length and repetition frequency. In some embodiments, the extracted features include features that are specific to each label triplet or apply to one or more of the sensor signals as a whole.

The exercise assistance system tags 1340 the label triplets in the sensor signals as repetitions or noise. The label triplets may be tagged manually by humans to ensure that the label triplets are tagged correctly. The exercise assistance system uses the extracted features and the tagged time labels to train 1350 a classification model that can identify label triplets as repetitions or as noise. The exercise assistance system can use the extracted features as input data and may use the tagged label triplets as verification data in a supervised machine-learning process. In some embodiments, the classification model is a support vector machine or a random decision forest.

FIG. 13B illustrates a method for applying a classification model for identifying repetitions in labeled sensor signals, in accordance with some embodiments. Alternate embodiments may include more, fewer, or different steps from the steps illustrated in FIGS. 13B, and the steps may be performed in a different order from the order described herein.

The exercise assistance system receives sensor signals 1360 from a movement measurement device, and labels sensor signals 1370 in accordance with the embodiments above. The received sensor signals can be different from the sensor signals used to train the classification model, as described with FIG. 13A. As described above, the exercise assistance system extracts 1380 features from the labeled sensor signals. The exercise assistance system applies 1390 the trained classification model to the labeled sensor signals using the extracted features as input data. By applying the classification model, the exercise assistance system identifies label triplets as repetitions or noise. In some embodiments, the classification model favors false positives over false negatives. In these cases, if the classification model is not confident whether a label triplet is noise, the classification model defaults to identifying the label triplet as a repetition.

Additional Configurations

Reference in the specification to "one embodiment" or to "an embodiment" means that a particular feature, structure, or characteristic described in connection with the embodiments is included in at least one embodiment. The appearances of the phrase "in one embodiment" or "an embodiment" in various places in the specification are not necessarily all referring to the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations or transformation of physical quantities or representations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device (such as a specific computing machine), that manipulates and transforms data represented as physical (electronic) quantities within the computer system memories or registers or other such information storage, transmission or display devices.

Certain aspects of the embodiments include process steps and instructions described herein in the form of an algorithm. It should be noted that the process steps and instructions of the embodiments can be embodied in software, firmware, or hardware, and when embodied in software, could be downloaded to reside on and be operated from different platforms used by a variety of operating systems. The embodiments can also be in a computer program product which can be executed on a computing system.

The embodiments also relate to an apparatus for performing the operations herein. This apparatus may be specially constructed for the purposes, e.g., a specific computer, or it may comprise a computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Memory can include any of the above and/or other devices that can store information/data/programs and can be transient or non-transient medium, where a non-transient or non-transitory medium can include memory/storage that stores information for more than a minimal duration. Furthermore, the computers referred to in the specification may include a single processor or may be architectures employing multiple processor designs for increased computing capability.

The algorithms and displays presented herein are not inherently related to any particular computer or other apparatus. Various systems may also be used with programs in accordance with the teachings herein, or it may prove convenient to construct more specialized apparatus to perform the method steps. The structure for a variety of these systems will appear from the description herein. In addition, the embodiments are not described with reference to any particular programming language. It will be appreciated that a variety of programming languages may be used to implement the teachings of the embodiments as described herein, and any references herein to specific languages are provided for disclosure of enablement and best mode.

In addition, the language used in the specification has been principally selected for readability and instructional purposes, and may not have been selected to delineate or circumscribe the inventive subject matter. Accordingly, the disclosure of the embodiments is intended to be illustrative, but not limiting, of the scope of the embodiments.

While particular embodiments and applications have been illustrated and described herein, it is to be understood that the embodiments are not limited to the precise construction and components disclosed herein and that various modifications, changes, and variations may be made in the arrangement, operation, and details of the methods and apparatuses of the embodiments without departing from the spirit and scope of the embodiments.

The invention claimed is:

1. A method comprising:
   receiving motion data from a motion measurement device, the motion data comprising a plurality of sensor signals from a plurality of sensors in the motion measurement device, the plurality of sensor signals describing a plurality of repetitions;
   generating a combination signal by computing a combination of the plurality of sensor signals;
   generating a labeling signal by passing the combination signal through a low pass filter;
   generating a first order derivative signal by computing the first order derivative of the labeling signal;
   generating a plurality of labels based on the labeling signal and the first order derivative signal, the plurality of labels comprising:
      a first label that identifies a beginning of a repetition of the plurality of repetitions,
      a second label that identifies an extremum of a repetition of the plurality of repetitions, and
      a third label that identifies an end of a repetition of the plurality of repetitions; and
   labeling the plurality of sensor signals based on the plurality of labels.

2. The method of claim 1, wherein the plurality of sensors includes at least one of an accelerometer, a gyroscope, a magnetometer, a GPS module, and an electric compass.

3. The method of claim 1, wherein the second label is generated by identifying a local extremum of the labeling signal.

4. The method of claim 1, wherein the first label and the third label of the plurality of labels are generated by identifying a local extremum of the first order derivative signal.

5. The method of claim 1, wherein labeling the sensor signals with the plurality of labels comprises identifying a plurality of label triplets, each label triplet comprising a first label of the plurality of labels that identifies a beginning of a repetition, a second label of the plurality of labels that identifies an extremum of the repetition, and a third label of the plurality of labels that identifies an end of the repetition, the first label, second label, and third label being chronologically sequential.

6. The method of claim 1, wherein the low pass filter comprises a cutoff frequency that is greater than an upper bound for a frequency of the plurality of repetitions.

7. The method of claim 1, wherein identifying the plurality of repetitions comprises applying a classification model that has been trained based on features extracted from the labeled sensor signals.

8. The method of claim 7, wherein identifying the plurality of repetitions comprises:
determining, by the classification model, whether a subset of the plurality of labels identifies a repetition of the plurality of repetitions; and
responsive to determining that the subset of the plurality of labels does not identify a repetition of the plurality of repetitions, identifying the subset of labels as identifying noise in the sensor signals.

9. The method of claim 1, wherein the movement measurement device is a wearable fitness device.

10. The method of claim 1, wherein each of the plurality of labels comprises a timestamp.

11. The method of claim 1, further comprising identifying the plurality of repetitions in the sensor signals based on the plurality of labels.

12. A non-transitory computer readable medium comprising instructions that, when executed by a processor, cause the processor to:
receive motion data from a motion measurement device, the motion data comprising a plurality of sensor signals from a plurality of sensors in the motion measurement device, the plurality of sensor signals describing a plurality of repetitions;
generate a combination signal by computing a combination of the plurality of sensor signals;
generate a labeling signal by passing the combination signal through a low pass filter;
generate a first order derivative signal by computing the first order derivative of the labeling signal;
generate a plurality of labels based on the labeling signal and the first order derivative signal, the plurality of labels comprising:
a first label that identifies a beginning of a repetition of the plurality of repetitions,
a second label that identifies an extremum of a repetition of the plurality of repetitions, and
a third label that identifies an end of a repetition of the plurality of repetitions;
label the plurality of sensor signals with the plurality of labels; and
identify the plurality of repetitions in the sensor signals based on the plurality of labels.

13. The computer readable medium of claim 12, wherein the plurality of sensors includes at least one of an accelerometer, a gyroscope, a magnetometer, a GPS module, and an electric compass.

14. The computer readable medium of claim 12, wherein the second label of the plurality of labels is generated by identifying a local extremum of the labeling signal.

15. The computer readable medium of claim 12, wherein the first label and the third label of the plurality of labels are generated by identifying a local extremum of the first order derivative signal.

16. The computer readable medium of claim 12, wherein the instructions for labeling the sensor signals with the plurality of labels further comprise instructions for identifying a plurality of label triplets, each label triplet comprising a first label of the plurality of labels that identifies a beginning of a repetition, a second label of the plurality of labels that identifies an extremum of the repetition, and a third label of the plurality of labels that identifies an end of the repetition, the first label, second label, and third label being chronologically sequential.

17. The computer readable medium of claim 12, wherein the low pass filter comprises a cutoff frequency that is greater than an upper bound for a frequency of the plurality of repetitions.

18. The computer readable medium of claim 12, wherein the instructions for identifying the plurality of repetitions comprises comprise instructions that, when executed, cause the processor to apply a classification model that has been trained based on features extracted from the labeled sensor signals.

19. The computer readable medium of claim 12, wherein the movement measurement device is a wearable fitness device.

20. The computer readable medium of claim 12, further comprising instructions that, when executed, cause the processor to identify the plurality of repetitions in the sensor signals based on the plurality of labels.

* * * * *